United States Patent
Harding (10) Patent No.: US 7,924,978 B2
(45) Date of Patent: Apr. 12, 2011

(54) SYSTEM AND METHOD FOR XRD-BASED THREAT DETECTION

(75) Inventor: Geoffrey Harding, Hamburg (DE)

(73) Assignee: Morpho Detection Inc., Newark, CA (US)

( * ) Notice: Subject to any disclaimer, the term of this patent is extended or adjusted under 35 U.S.C. 154(b) by 31 days.

(21) Appl. No.: 12/390,861

(22) Filed: Feb. 23, 2009

(65) Prior Publication Data

US 2009/0213989 A1 Aug. 27, 2009

Related U.S. Application Data

(60) Provisional application No. 61/030,599, filed on Feb. 22, 2008.

(51) Int. Cl.
*G21K 1/06* (2006.01)

(52) U.S. Cl. .............................. 378/84; 378/87

(58) Field of Classification Search .............. 378/90, 378/71, 84, 86, 87, 145–153
See application file for complete search history.

(56) References Cited

U.S. PATENT DOCUMENTS

| | | | | |
|---|---|---|---|---|
| 4,541,107 | A * | 9/1985 | Rossi | 378/146 |
| 4,773,087 | A * | 9/1988 | Plewes | 378/146 |
| 5,787,145 | A | 7/1998 | Geus | |
| 7,065,175 | B2 | 6/2006 | Green | |
| 7,092,485 | B2 | 8/2006 | Kravis | |
| 7,164,747 | B2 | 1/2007 | Ellenbogen et al. | |
| 7,321,652 | B2 | 1/2008 | Yokhin et al. | |

FOREIGN PATENT DOCUMENTS

WO 2008033620 A2 3/2008

* cited by examiner

*Primary Examiner* — Hoon Song
(74) *Attorney, Agent, or Firm* — Armstrong Teasdale LLP (57) ABSTRACT

System and method for XRD-based threat detection. An object is scanned with a first threat detection system. One or more alarm objects are identified. Data about the one or more alarm objects is passed from the first threat detection system to a second threat detection system and is used to move and/or to rotate the object in a predetermined ray path that decreases attenuation of scattered x-ray radiation. Also disclosed is a secondary collimator for XRD-based false alarm resolution in computed tomography {"CT"} threat detection systems. The secondary collimator comprises one or more slit apertures configured to provide a multi-angle capability that extends a range of momenta for which XRD intensities are measured for a predetermined range of photon intensities.

11 Claims, 9 Drawing Sheets

SYSTEM AND METHOD FOR XRD-BASED THREAT DETECTION

CROSS-REFERENCE TO RELATED APPLICATIONS

This application claims benefit under 35 U.S.C. §119(e), to prior-filed, U.S. provisional patent application Ser. No. 61/030,599, filed on Feb. 22, 2008, which is hereby incorporated by reference in its entirety.

STATEMENT REGARDING FEDERALLY SPONSORED RESEARCH OR DEVELOPMENT

Not Applicable

NAMES OF PARTIES TO A JOINT RESEARCH AGREEMENT

Not Applicable

BACKGROUND

1. Field of the Invention

The field of the invention relates to computed tomography ("CT")-based threat detection systems generally, and more particularly to certain new and useful advances in using X-ray Diffraction ("XRD") to resolve false alarms generated by a megavoltage CT threat detection system, of which the following is a specification, reference being had to the drawings accompanying and forming a part of the same.

2. Discussion of Related Art

Megavoltage CT has been developed for inspection and screening of shipping containers, as it provides a high-resolution data 3-D data set of the density and approximate atomic number distribution inside the container. That said, Megavoltage CT is not material-specific, and has been found to generate a significant number of false alarms for some cargo categories. Some of these alarms can be cleared employing On-Screen Alarm ("OSAR") protocols. The remaining alarms, however, need to be cleared by a secondary technique or failing that, in a worst-case scenario, containers that generate an alarm must be manually inspected. It is desirable to avoid employing a secondary technique or manually inspecting an alarm as both operations are extremely costly.

XRD is a material-specific analysis technique that permits the local diffraction properties of a selected volume element (voxel) of an extended object (e.g. a suitcase, a shipping container, and the like) to be determined. The idea of operating an XRD system as a second inspection modality following a first CT investigation as a way of reducing the false alarm rate in airport baggage screening has been generically outlined in the scientific literature, but the mere mention of this idea left many problems unsolved.

One such problem is whether and how high density metals ("HDMS") and/or shielded special nuclear materials ("SNMs") present in shipping containers, passenger baggage, and the like can be detected using a CT-based threat detection system in combination with an XRD-based threat detection system. Another problem is how to optimize an XRD threat detection system to decrease its total X-ray attenuation. Another problem is how to permit simultaneous XRD imaging from a one-dimensional array of object voxels.

Accordingly, an improved threat detection system is needed that detects shielded SNMs, decreases or eliminates false alarms, and that determines a minimum attenuation path through an object, such as a shipping container, a piece of baggage, and the like. Additionally, an improved secondary collimator is needed that enables simultaneous XRD imaging from a one-dimensional array of object voxels.

BRIEF SUMMARY OF THE INVENTION

The subject matter described, shown, and claimed herein is believed to be novel and inventive in that it overcomes many of the drawbacks and disadvantages associated with prior threat detection systems and provides unique solutions for at least the long-felt needs identified above. Additionally, the subject matter described, shown, and claimed herein offers detection synergy in that a single improved threat detection system can be configured to detect both SNMs and conventional explosives, including organic, home-made explosives ("HMEs"), and liquids.

In developing the subject matter described, shown, and claimed herein it was discovered that high density metals ("HDMs"), also called "high-Z metals," where "Z" is a material's atomic number, have cubic crystalline structures, and that X-ray Diffraction can be used to preferentially select high-Z metals through the atomic Z2 coherent scatter intensity effect. It was also discovered that a special subset of HDMs called Special Nuclear Materials ("SNMs"), have non-cubic lattice structures, and that the SNMs' non-cubic lattice structures enable rapid, accurate, and material-specific XRD-based differentiation. Examples of SNMs include uranium and plutonium. Additionally, the three-dimensional ("3-D") data obtained by first scanning an object, such as a shipping container, a piece of baggage, and the like, with a CT-based threat detection system can be used to determine a minimum X-ray attenuation path through the object. Advantageously, the minimum X-ray attenuation path can thereafter be used to obtain an accurate XRD measurement of a diffraction profile of an alarm region previously identified by the Megavolt CT-based threat detection system.

Accordingly, an XRD-based threat detection system, and method of operating the same, are disclosed herein as being configured to use a previously determined minimal X-ray attenuation path to detect HDMs generally, and shielded SNMs in particular, with minimal or no false alarms.

An improved secondary collimator can be constructed by including therein a continuous spiral slit aperture. The continuous spiral slit aperture provides a multi-angle capability that significantly extends the range of momenta for which XRD intensities are measured for a predetermined range of photon intensities.

Such an improved secondary collimator enables simultaneous XRD imaging from a one-dimensional array of object voxels. Advantageously, the simultaneous XRD imaging can be performed using only the high-energy end of a source spectrum.

Moreover, XRD intensity profiles over a limited energy range can be super-imposed on one another to derive an XRD intensity profile over an extended momentum range. Using the improved secondary collimator having the continuous spiral secondary aperture allows an XRD-based threat detection system having multiple X-ray detectors to resolve multiple alarms simultaneously, which were previously identified by a CT-based threat detection system. These two innovations lead to a higher signal-to-noise ratio in the XRD profile, which increases the detection rate and reduces the false alarm rate.

An XRD-based threat detection system having multiple X-ray detectors has a significant advantage over XRD-based threat detection systems that have only a single X-ray detector. To resolve multiple alarms using a single detector XRD-based threat detection system, the single detector must be moved multiple times—each time to a position that corresponds to a particular alarm. In contrast, a multiple detector XRD-based threat detection system equipped with the improved secondary collimator having a continuous spiral secondary aperture, can resolve multiple alarms simultaneously and while keeping each of the multiple X-ray detectors stationary.

Accordingly, an improved secondary collimator, a method of using the same, and a threat detection system including the same are described, shown, and claimed herein.

Other features and advantages of the subject matter described, shown, and claimed herein will become apparent by reference to the following description taken in connection with the accompanying drawings.

BRIEF DESCRIPTION OF THE DRAWINGS

Reference is now made briefly to the accompanying drawings, in which.

Like reference characters designate identical or corresponding components and units throughout the several views, which are not to scale unless otherwise indicated.

DETAILED DESCRIPTION

Specific configurations and arrangements of the claimed invention, discussed below with reference to the accompanying drawings, are for illustrative purposes only. Other configurations and arrangements that are within the purview of a skilled artisan can be made without departing from the spirit and scope of the appended claims.

CT-Based Threat Detection

Figure 1:
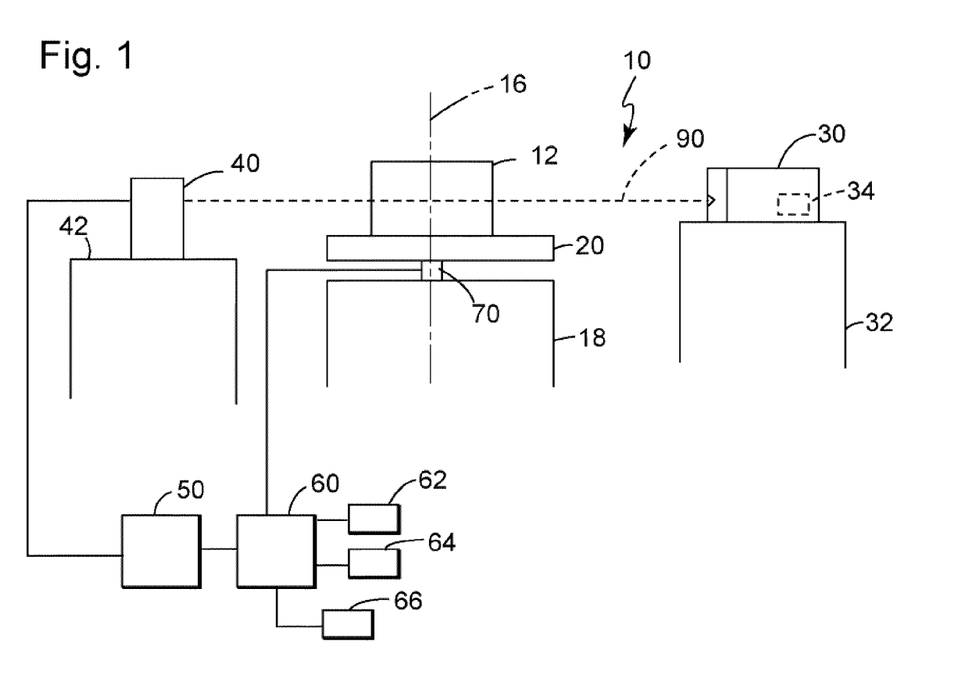
FIG. 1 is a schematic illustration of a first threat detection system, previously disclosed in co-pending, related, and unpublished U.S. patent application Ser. No. 11/654,251 filed on Jan. 17, 2007.

FIG. 1 is a schematic illustration of a first threat detection system 10, which is configured to scan an object 12, such as a shipping container, a piece of baggage, and the like, to identify the contents of and/or determine a type of one or more materials contained in the object 12.

In one embodiment, the first threat detection system 10 is a Megavolt CT-based threat detection system, such as that previously disclosed in co-pending, related, and unpublished U.S. patent application Ser. No. 11/654,251 filed on Jan. 17, 2007. However, any suitable CT-based threat detection system may be used.

The object 12 rests on a movable platform 20, which, together with the object 12, can be raised and lowered vertically along, and/or rotated about, a vertical axis 16 by an actuator 70, which is coupled with, or supported by, a frame 18. The actuator 70 may also be configured to move the movable platform 20, and the object 12, along a horizontal axis 90. A computer 60 may be coupled with the actuator 70 and configured to control the vertical, rotational, and/or horizontal movement of the platform 20 and the object 12 thereon. The actuator 70 may be any suitable drive assembly known to those skilled in the art and guided by the teachings herein provided.

A frame 32 may support at least one radiation source 30, which is configured to transmit at least one beam of radiation 95, such as a cone beam, through object 12, as described in greater detail below. In one embodiment, a radiation source 30 is a X-ray source, such as a Megavolt X-ray generator.

In one embodiment, a plurality of X-ray sources 30 are fixedly positioned with respect to platform 20 and configured to emit radiation of different energy distributions. Alternatively, each X-ray source 30 is configured to emit radiation of selective energy distributions, which can be emitted at different times.

In a particular embodiment, the first threat detection system 10 utilizes multiple energy inspection to obtain an attenuation map for object 12. In a multiple energy system, such as a dual energy system, a first or low energy source generates radiation having an energy distribution of about 2 MV to about 6 MV and a second or high energy source generates radiation having an energy distribution of about 6 MV to about 20 MV. It is apparent to those skilled in the art and guided by the teachings herein provided that the first energy source may generate radiation having an energy distribution less than about 2 MV and/or greater than about 6 MV and/or the second energy source may generate radiation having an energy distribution less than about 6 MV and/or greater than about 20 MV.

In addition to the production of CT images, multiple-energy scanning enables the production of density maps and atomic number of the object contents. This information allows for an improved identification of the materials contained in object 12. For example, it allows for accurately distinguishing high-density tungsten from uranium. In one embodiment, the dual energy scanning of object 12 includes inspecting object 12 by scanning object 12 at the low energy and then scanning object 12 at the high-energy. The data is collected for the low-energy scan and the high-energy scan to reconstruct the CT, density and/or atomic number images of object 12, which are used to identify a type of material or contraband in the object 12, as described in greater detail below.

In an alternative embodiment, X-ray source 30 includes a linear accelerator 34 that produces radiation pulses of the same or varying energies. In this embodiment, linear accelerator 34 generates the low energy x-rays and the high energy x-rays in a high speed switching mode or interlaced mode such that object 12 is scanned only one time. This approach allows for higher throughput. In further alternative embodiments, X-ray source 30 includes a suitable electrostatic accelerator, a microtron or a betatron or any other type of X-ray source.

In one embodiment, object 12 is scanned with at least one energy distribution.

At least one X-ray detector 40 is fixedly positioned with respect to frame 18 and/or platform 20. In one embodiment, X-ray detector 40 is fixedly positioned with respect to a second side of frame 18 and/or platform 20 opposing the platform first side. In a particular embodiment, X-ray detector 40 is mounted to a second tower 42 positioned with respect to base 14, as shown in FIG. 1. X-ray detector 40 is configured to detect radiation emitted from X-ray source 30 and transmitted through object 12. X-ray detector 40 is configured to cover an entire field of view or only a portion of the filed of view. Upon detection of the transmitted radiation, X-ray detector 40 generates a signal representative of the detected transmitted radiation. The signal is transmitted to a data collection system 50 and/or the computer processor 60 for processing.

The first threat detection system 10 is configured to operate in either of a step-and-shoot mode and a helical mode. In the step-and-shoot mode, the radiation source 30 is fixedly positioned with respect to object 12 to be scanned. Thereafter, one or more radiation beams 95 may be transmitted through the object 12 to impinge the detector 40, with or without the object 12 rotating during beam transmissions or between beam transmissions. In one embodiment, object 12 is continuously rotated during the step-and-shot mode while the frame 18 remains stationary. Alternatively, in the helical mode, platform 20 is continuously rotated as frame 18 is moved along the vertical axis 16.

Use of the first threat detection system 10 facilitates obtaining a large number of precise X-ray views, which are then used to reconstruct a volumetric image of the object 12. The image is a mapping of the CT number for each volume element regardless of the superposition of objects or materials within object 12. In one embodiment, an imaging system is coupled to X-ray detectors 40 to process the image data for producing a two-dimensional or three-dimensional map of the container and its contents. The reconstructed images are processed to determine a CT number, density and/or atomic number of object 12 being scanned. Analysis of these images facilitates determining a type of material contained in object 12, for example.

In one embodiment the imaging system includes a data collection system 50 that is operatively coupled to and in signal communication with X-ray detector 40. The data collection system 50 is configured to receive the signals generated and transmitted by X-ray detector 40.

A computer processor 60 is operatively coupled to data collection system 50, and to the actuator 70. The processor 60 is configured to produce or generate an image of object 12 and its contents, and to process the produced image for facilitating determining what material(s) are in the object 12.

More specifically, in one embodiment data collection system 50 and/or processor 60 produces at least one attenuation map based upon the signals received from X-ray detector 40. Utilizing the attenuation map(s), at least one image of the contents is reconstructed and a CT number, a density and/or an atomic number of the contents is inferred from the reconstructed image(s). When data is collected using a single energy mode, the CT image is analyzed. When data is collected using a multiple energy mode, two or more CT images of the cargo are produced. Based on these CT images, density and/or atomic maps of the cargo can be produced. The CT images, the density and/or atomic number images are analyzed to infer the presence of contraband such as explosives, special nuclear and shielding materials, and/or to verify information listed in one or more cargo manifests.

In alternative embodiments, one processor 60 or more than one processor 60 may be used to generate and/or process the object image. In one embodiment, system 10 also includes a display device 62, a memory device 64 and/or an input device 66 operatively coupled to data collection system 50 and/or processor 60.

As used herein, the term "processor" is not limited to only integrated circuits referred to in the art as a processor, but broadly refers to a computer, a microcontroller, a microcomputer, a programmable logic controller, an application specific integrated circuit and any other programmable circuit. The term "processor" may also include a storage device and/or an input device, such as a mouse and/or a keyboard.

XRD-Based Threat Detection System

Figure 2:
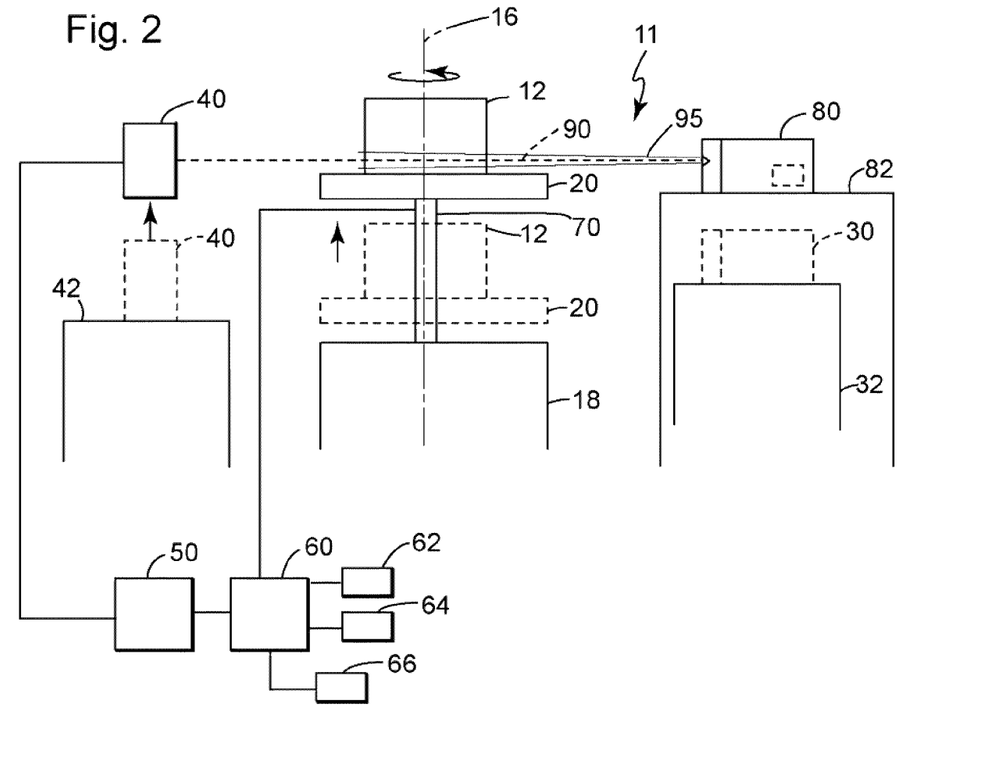
FIG. 2 is a schematic illustration of an embodiment of a second threat detection system.

FIG. 2 is a schematic illustration of an embodiment of a second threat detection system 11. In one embodiment, the second threat detection system 11 is a XRD-based threat detection system. Much of FIG. 2 is identical to FIG. 1. For example, descriptions of the vertical axis 16, horizontal axis 90, and components 18, 32, 42, 50, 60, 62, 64, 66, and 70, which appear in FIG. 2 were provided above, and are not repeated here.

FIG. 2 additionally shows a second radiation source 80 supported by a frame 82. FIG. 2 also shows how the platform 20 can be moved by the actuator 70 to bring a suspicious area of the object, which was previously identified by the first (CT-based) threat detection system 10, into alignment with a primary beam aperture of the second radiation source 80. In an embodiment, the second radiation source 80 is a XRD radiation source. FIG. 2 further illustrates how the detector 40 can be moved relative to the second radiation source 80.

The first threat detection system 10 and the second threat detection system 11 may be combined into a single integrated threat detection system. Alternatively, the first threat detection system 10 and the second threat detection system 11 may stand alone from each other. If formed as stand-alone systems, each threat detection system 10, 11 may be configured to receive, analyze, and/or operate using scan and/or image data obtained by the other.

XRD-Based Resolution of False Alarms

Figure 3:
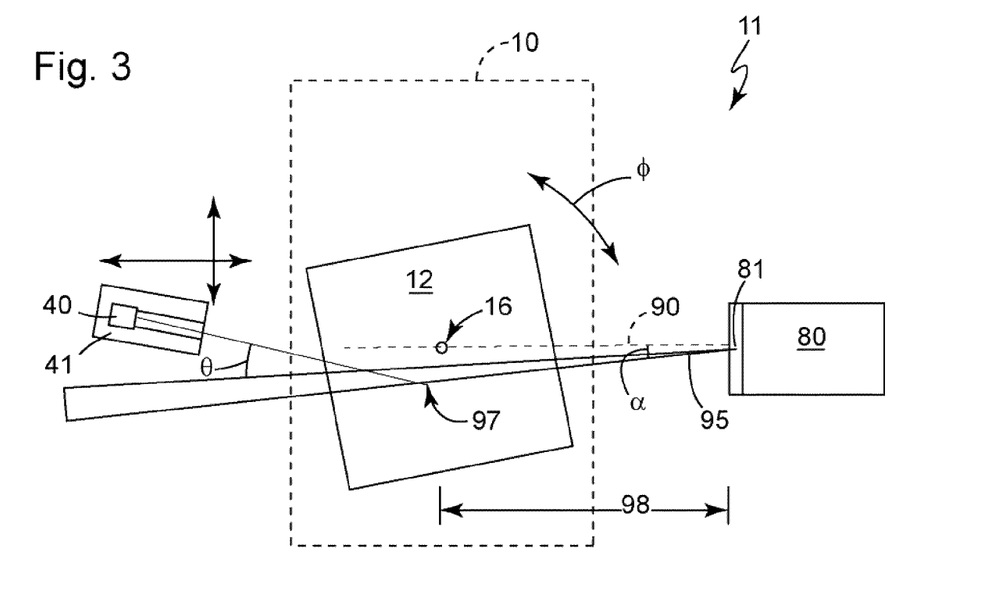
FIG. 3 is another schematic illustration of an embodiment of the second threat detection system of FIG. 2.

FIG. 3 is another schematic illustration of an embodiment of the second threat detection system 11 of FIG. 2. In FIG. 3, the first threat detection system 10 is indicated by a dashed rectangle. As depicted, an object 12, positioned between the second radiation source 80 the detector 40, is rotatable at a rotation angle $\Phi$ about the vertical axis 16. The radiation beam 95, which may be a cone beam, may form a ray angle $\alpha$ with the horizontal axis 90. The radiation source 80 may include an adjustable diaphragm 81. The detector 40 may include collimator/shielding 41. A suspicious area, also called an "alarm region," 97 may be identified in the object 12 along the ray path at a distance 98, measured in one or more dimensions, from the second radiation source 80.

In an embodiment, the detector 40 is a spectroscopic photon counting detector, such as, but not limited to, a hyper-pure Ge detector or a room-temperature semi-conductor such as HgI2 or CdTe. The detector 40 is focused at a small angle of scatter $\theta$. In one embodiment, the scatter angle $\theta$ may range from about 0.05 radians to about 0.01 radians relative to the suspicious area 97. The small angle of scatter is believed to be necessary to secure an accurate measurement of a XRD profile over a momentum region of about, and including, 1 nm$^{-1}$, where the Bragg peaks of significance for material analysis are situated. In one embodiment, the detector 40 is one or more detectors placed at fixed angles relative to one of the vertical axis 16 and the horizontal axis 90.

In one embodiment, the second radiation source 80 may be, but is not limited to, a DC electron impact bremsstrahlung source. In one embodiment, the second radiation source 80 may be, but is not limited to, a liquid metal anode X-ray source. Advantages of using a liquid metal anode X-ray source as compared to a linac XD-ray source include, but are not limited to: a more compact radiation shield, simpler collimation elements, and reduced detector cross-talk.

At the time of this filing, the highest energy, commercially available DC electron impact bremsstrahlung source operates at a potential of about 850 KV. However, other X-ray sources operating at even higher voltages, i.e., up to and including about 8 MeV, such as linacs, betatrons, and the like, may also be used as the second radiation source 80, provided arrangements are made to compensate for, or eliminate, dead time problems in the detector 40 that are caused by concentrated bunches of photons emitted in short pulse times on the order of about 5 µs.

It should be noted that the first radiation source 30, used in the CT-based threat detection system 10, may be, but need not be, different from the second radiation source 80, used in the XRD-based threat detection system 11, because of the pulsing and large focal spot of the CT-based threat detection system 10 and because the higher energy of the first radiation source 30 reduces the observation angle(s). If a different second radiation source 80 is used, it should be on the side of, or above, or below the first radiation source 30. In one embodiment, the second radiation source 80 is positioned relative to the first radiation source 30 to maintain or decrease the translational range requirement.

Following analysis of the CT images that resulted from operating the first threat detection system 10, at least one of a user, the DAS 50, and the computer processor 60 selects one or more suspicious areas (97 in FIG. 3) of, or in, the object 12, which may be called "alarm areas," or "alarms,"—and which may contain one or more "alarm objects"—for a more detailed scan, which a second threat detection system 11 thereafter performs. A non-limiting example of a second threat detection system 11 is a XRD-based threat detection system.

In one embodiment, the second threat detection system 11 is configured to receive, or use, all or part of the scan and/or image data, and/or other information, obtained by the first threat detection system 10. The scan and/or image data obtained by the first threat detection system 10, and received and/or used by the second threat detection system 11, may be one-dimensional or multi-dimensional, e.g., two-dimensional ("2-D"), three-dimensional ("3-D"), and so forth, and may be used to determine a minimal X-ray attenuation path that is subsequently used to perform a XRD-based scan of the one or more selected suspicious areas of the object 12. A "minimal X-ray attenuation path" is a predetermined ray path that decreases attenuation of x-rays emitted by the second threat detection system. This predetermined ray path is calculated, or determined, by a computer processor using data about one or more suspicious areas of the object 12, as described below. To obtain an optimal signal and/or to increase throughput, the object 12 is moved and/or rotated to place the alarm object in the minimal X-ray attenuation path for scanning by the second threat detection system 11.

When the first threat detection system 10 raises an alarm, i.e. identifies one or more suspicious areas in the object 12, various data about the one or more suspicious areas are transmitted to the second threat detection system 11. These data include, but are not limited to:

(a) a single-dimensional geometrical position of the suspicious area 97 and/or alarm object(s) in the object 12;
(b) a multi-dimensional geometrical position of the suspicious area 97 and/or alarm object(s) in the object 12;
(c) a geometry of a ray path from the x-ray source 30,80 to the detector 40 in a horizontal plane that contains the suspicious area 97 and/or alarm object(s), wherein the geometry of the ray path decreases a total X-ray attenuation;
(d) a value of an object density integrated along this predetermined ray path; and
(e) a number of suspicious areas 97 and/or alarm object(s) and their spatial distribution along this predetermined ray path.

Figure 4:
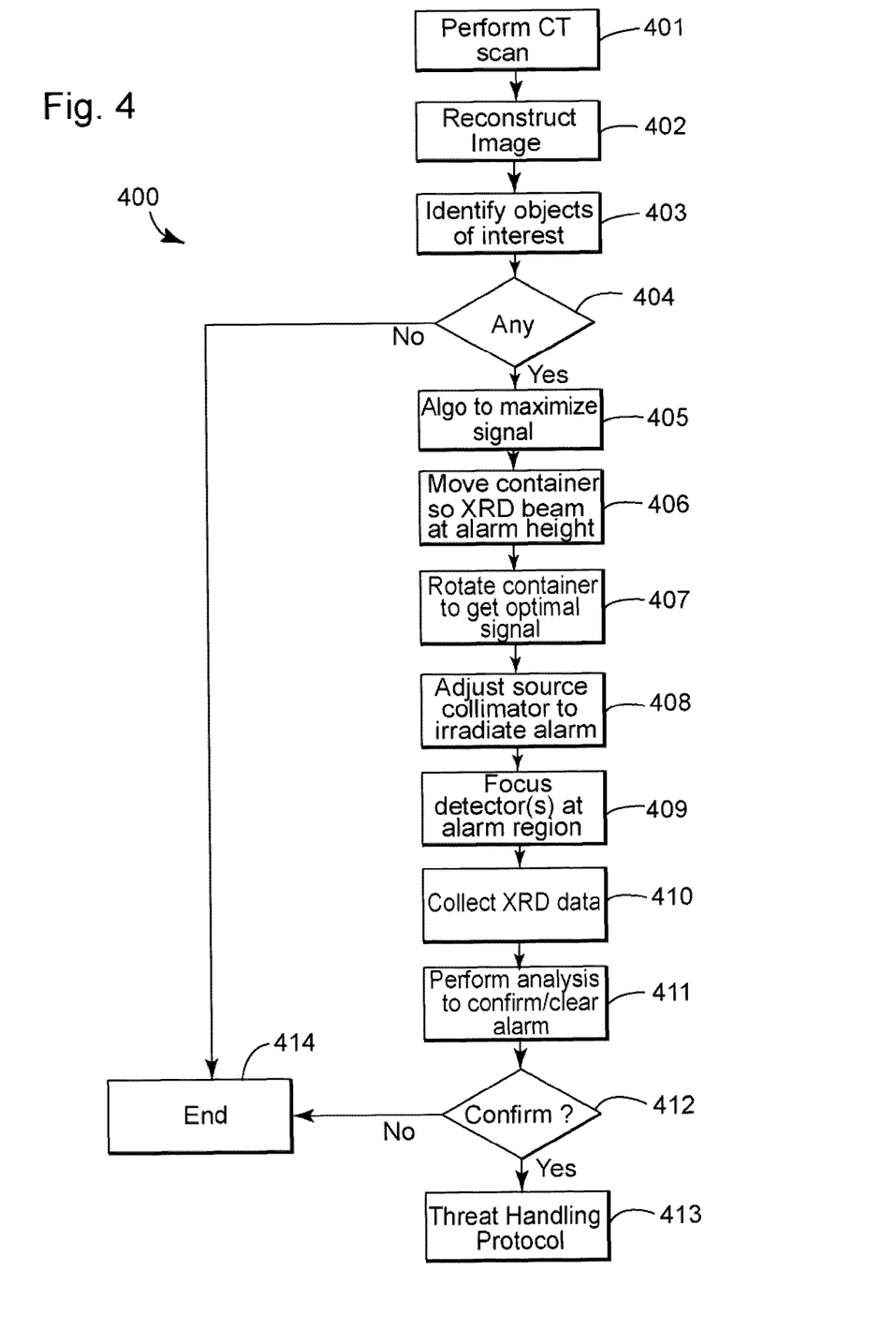
FIG. 4 is a flowchart illustrating a method of operating the second threat detection system of FIGS. 2 and 3.

FIG. 4 is a flowchart illustrating a method of operating the second threat detection system of FIGS. 2 and 3. Referring briefly to FIGS. 1, 2, 3, and 4, the functional blocks of the flowchart 400 each represent one or more actions that may be performed by the computer processor 60 when the computer processor 60 executes machine-readable instructions. Unless otherwise indicated, the actions represented by the functional blocks of the flowchart 400 may be performed simultaneously or in any suitable order. The machine-readable instructions executed by the computer processor 60 may be stored in the computer-readable memory 64.

Referring still to FIGS. 1, 2, 3, and 4, the method 400 may begin, as represented by functional block 401, by performing a CT scan of the object 12, as described above. As represented by functional block 402, once the CT scan is complete, the method 400 may further include reconstructing one or more CT images. As represented by functional block 403, once the CT scan is complete, the method 400 may further include identifying one or more suspicious areas 97, or alarm objects (501, 502, 503 in FIG. 5). As represented by functional block 404, a decision is made. If no suspicious areas 97 or alarm objects 501, 502, 503 are present, the method 400 ends, as represented by functional block 414.

Figure 5:
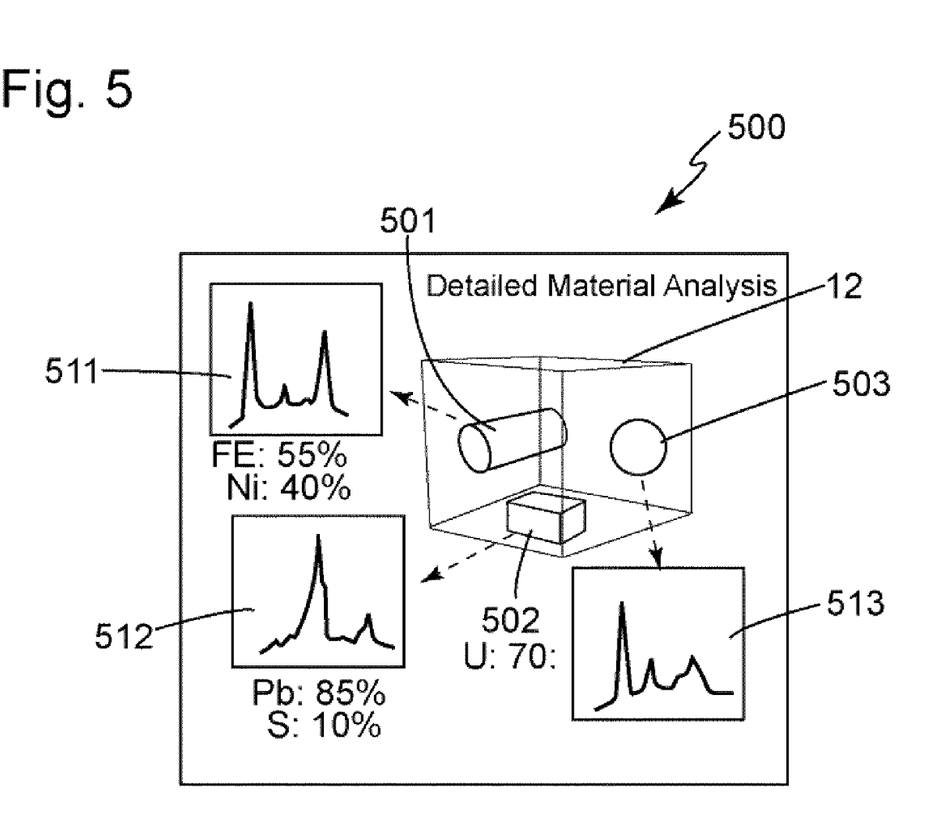
FIG. 5 is a diagram illustrating how detailed material analysis may be performed using a XRD-based threat detection system to detect one or more HDMs.

If one or more suspicious areas 97 or alarm objects 501, 502, 503 are identified, the method 400 further includes, as represented by functional block 405, increasing and/or maximizing the signal quality using one or more pre-determined signal processing algorithms, which are believed to be within the ability of a skilled artisan to create and implement without undue experimentation. Accordingly, detailed explanations of such signal processing algorithms are not provided here, except to say that a computer processor 60 determines for all possible rays intersecting the suspicious area 97 in the horizontal measurement plane a single ray path that decreases and/or decreases the total X-ray attenuation for x-rays emitted by the second threat detection system 11 and/or scattered from the object 12 and/or one or more alarm objects. It does this using the 3-D distribution of attenuation coefficient data that are reconstructed following the CT scan. The ray path that decreases the total attenuation is defined by an angular position of the object 12 (e.g., the rotation angle, or projection angle, Φ, and by an angular coordinate of the primary ray beam from the second radiation source 80, i.e., by the ray angle α. To select the X-ray beam from the source having the ray angle α, the adjustable diaphragm(s) 81 may be moved.

Referring again to FIG. 4, the method 400 may further include, as represented by the functional block 406, moving the object 12 on the platform 20 to a vertical position at which the suspicious area 97 is in the measurement plane of the second radiation source 80. As represented by the functional blocks 407, the method 400 may further include rotating the object 12 to improve a signal-to-noise ratio. As represented by the functional block 408, the method may further include adjusting the second radiation source 80 to irradiate the suspicious area 97 and/or one or more alarm objects. As represented by the functional block 409, the method may further include focusing the detector(s) 40 at the suspicious area 97, e.g., in alignment with the predetermined ray path. The actions represented by each of the functional blocks 407, 408, and 409 may include aligning a second radiation source 80 and the suspicious area 97 along the predetermined ray path, determined at functional block 405, to decrease the total X-ray attenuation.

As represented by the functional block 410, the method 400 may include collecting XRD data indicative of x-ray radiation scattered from the irradiated suspicious area 97 and/or one or more alarm objects. As represented by the functional block 411, the method may further include analyzing a signal output from the x-ray detector, of the second threat detection system 11, to confirm or clear the one or more alarm objects.

As represented by the functional block 412, the method 400 may include making a decision. If the alarm object is cleared, i.e., determined to be a non-threat, the method 400 may end. If the alarm is confirmed, i.e., the alarm object determined to be suspicious and/or a threat, the method 400 may further include executing a pre-determined threat-handling protocol, as represented by the functional block 413.

FIG. 5 is a diagram 500 illustrating how a detailed material analysis may be performed using a XRD-based threat detection system to detect one or more HDMs. Referring to FIGS. 1, 2, 3, and 5, in the diagram 500, three alarm objects 501, 502, 503 have been identified in an object 12 by a first CT-based threat detection system 10. Thereafter, interrogation and analyses of each alarm object 501, 502, 503 by a second XRD-based threat detection system 11 produced the respective diffraction profiles 511, 512, and 513, which identify the materials and compositions of materials that comprise each alarm object 501, 502, 503. For example, alarm object 501 was determined to comprise 55% FE and 40% Ni; alarm object 502 was determined to comprise 85% Pb and 10% S; and alarm object 503 was determined to comprise 70% U.

A basis for performing the XRD-based resolution of false alarms is that the atomic coherent scatter cross section scales as $Z^2$, thus enhancing the signal from high Z elements; whereas uranium and plutonium, alone among all high density metals, have non-cubic crystal structures. Their XRD patterns differ greatly from those of other high Z metals such as lead, which have cubic crystal structures. It is believed that expected measurement parameters, such as XRD signals, spatial resolutions, photon fluxes and measurement time can be performed by a skilled artisan without undue experimentation.

Secondary Collimator

In addition to the "single-point" detection system described above, a multipoint, multi-angle detection system has been invented for XRD-based resolution of false alarms. The multipoint, multi-angle detection system has the advantages of recording diffraction profiles from all voxels irradiated by the primary beam simultaneously (multipoint), and also of recording diffraction profiles simultaneously at several discrete angles (multi-angle) thus extending the momentum range over which a XRD profile is measured.

Consequently, the resulting XRD profile benefits from improved signal-to-noise ratio. This has the effects of increasing accuracy of detection and reducing false alarms.

Figure 6:
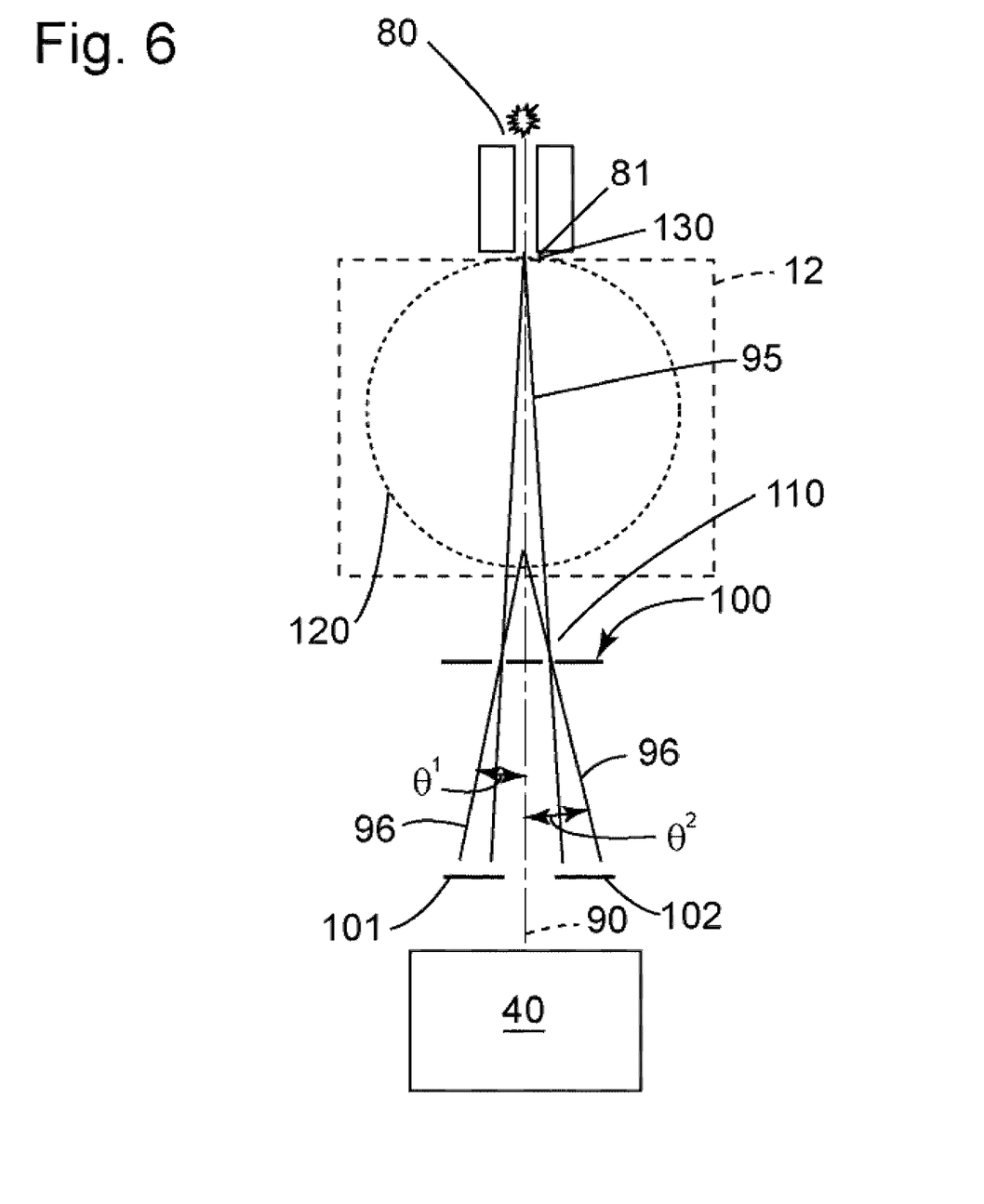
FIG. 6 is a schematic illustration of an improved XRD-based threat detection system that includes multiple X-ray detectors and an embodiment of an improved secondary collimator.

FIG. 6 is a schematic illustration of an improved XRD-based threat detection system 11 that includes multiple X-ray detectors 40, 101, 102 and an embodiment of an improved secondary collimator 100 having one or more slit apertures 110 formed therein. The secondary collimator 110 is positioned between the second radiation source 80 and the detector 40. In one embodiment, the secondary collimator comprises one or more slit apertures that are configured to provide a multi-angle capability that extends a range of momenta for which XRD intensities are measured for a predetermined range of photon intensities.

In one embodiment, multiple scatter detectors 101, 102 are positioned between the secondary collimator 100 and the detector 40. Each of the multiple scatter detectors 101, 102 are disposed at predetermined scatter angles $\theta^1$ and $\theta^2$, respectively, with respect to the axis 90, to capture photons scattered from a scan area 120 along ray paths 96, which pass through the secondary collimator's one or more slit apertures 110. The scan area 120 may include all or part of a suspicious area 97, or alarm object(s), that a previous CT scan identified in an object 12. As shown in FIG. 6, the object 12 and the scan area 120 are positioned between the secondary collimator 100 and the second radiation source 80.

Referring briefly to FIGS. 3 and 6, a primary aperture 130 is formed in the adjustable diaphragm 81, which is positioned between the second radiation source 80 and the object 12. A cone-shaped beam, or other shaped beam, of X-ray radiation 95 is emitted from the second radiation source 80 and transmitted through the scanning area 120 of the object 12. After traversing the scanning area 120, the beam of X-ray radiation 95 passes through the one or more slit apertures 110 of the secondary collimator 100. A first portion of the beam of X-ray radiation 95 impinges the detector 40; other portions of the beam of X-ray radiation 95 scatter along ray paths 96 to impinge the multiple scatter detectors 101, 102.

For simplicity the proposed collimation scheme is shown in FIG. 6 with only two detector systems, i.e., detector 40 and the multiple scatter detectors 101, 102, although many more detectors are possible. Rays 95 scattered at a small angle from the front of the object 12, nearest to the second radiation source 80, impinge on the secondary collimator 100 in the form of a slit aperture 110, which is formed in a material having a high atomic number, Z, such as lead.

Those rays 95 that pass through the slit opening are incident on a pixellated detector 40. In an embodiment, the pixels have dimensions on the order of about 250 microns. The relative positions of the detector 40 and the secondary collimator 100 and the second radiation source 80 define the axis 90, which intersects the primary beam 95 at an origin coordinate of the scatter event.

The neighboring multiple scatter detectors 101, 102 record scatter from slightly different positions along the primary beam 95. Hence an array of scatter detectors 101, 102 that is large enough to encompass all the scatter rays 96 from the object 12 will measure scattering from a complete line of volume elements (voxels) simultaneously. This is a big advantage over the single detector system, since it is no longer necessary to move the detector to the correct position. Instead, when there are several suspicious areas 97 in the object 12; they can all be resolved simultaneously.

Referring still to FIG. 6, rays 96 from different voxels along the primary beam 95 have slightly different angles of scatter. The scatter angle, $\theta$, is obtained from simple geometry as in the following equation:

Equation 1

$$\theta_i = \tan^{-1}\left(\frac{a_i}{S - x_v}\right) \qquad (1)$$

In this equation, $a_i$ is the distance of the ith secondary collimator slit from the primary beam (x) axis; S is the position (x coordinate) of the secondary collimator referred to the x-ray source and $x_v$ is an x coordinate of the voxel in which scattering originates.

Figure 7:
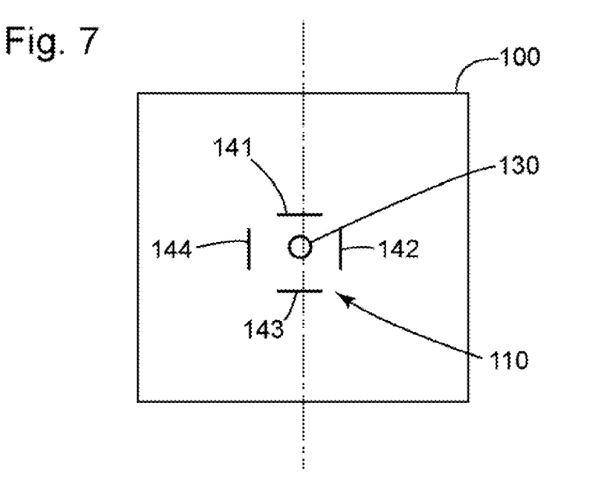
FIG. 7 is a top view of an embodiment of the improved secondary collimator of FIG. 6.

FIG. 7 is a top view of an embodiment of the secondary collimator 100 of FIG. 6. FIG. 7 illustrates multiple slit apertures 110 formed in a single secondary collimator 100 and arranged at different distances from a primary beam aperture and/or axis 130. The multiple slit apertures 110 include: a first slit aperture 141, a second slit aperture 142, a third slit aperture 143, and a fourth slit aperture 144. The first slit aperture 141 is arranged closest to the primary beam aperture 130. The first slit aperture 141 is also orthogonal to the second slit aperture 142, parallel to the third slit aperture 143, and orthogonal to the fourth slit aperture 144.

The second slit aperture 142 is arranged further from the primary beam aperture/axis 130 than the first slit aperture 141. The third slit aperture 143 is arranged further from the primary beam aperture/axis 130 than the second slit aperture 142. Additionally, the fourth slit aperture is arranged further from the primary beam aperture/axis 130 than the third slit aperture 143.

Figure 8:
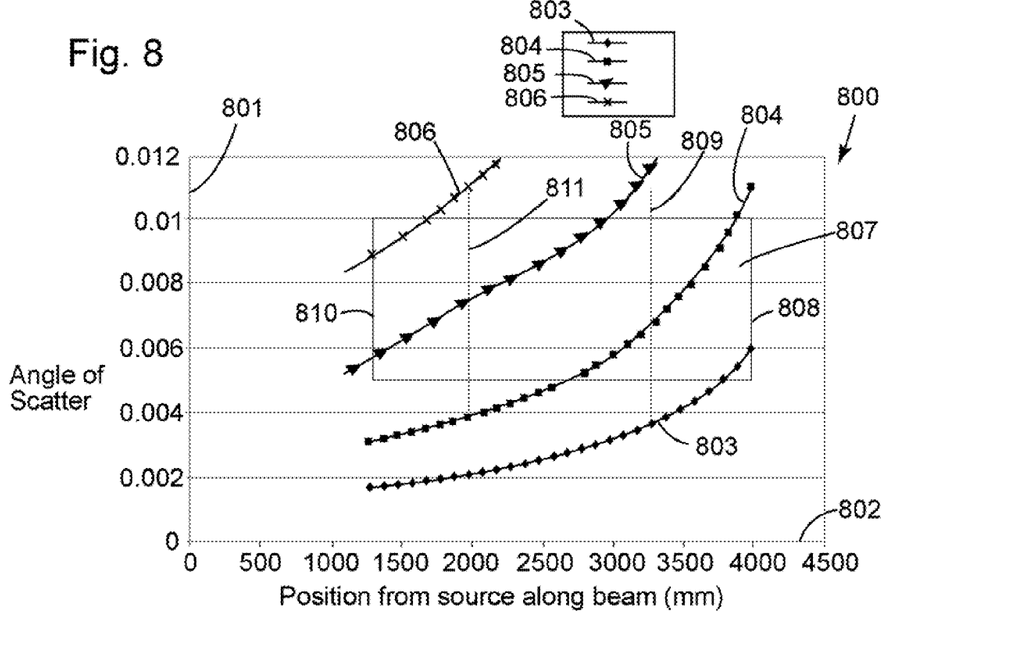
FIG. 8 is a graph that plots angles of scatter versus position from a radiation source along an X-ray beam for each of the four slit apertures illustratively shown in FIG. 7.

FIG. 8 is a graph 800 that plots angles of scatter 801 versus position 802 from a radiation source along an X-ray beam for each of the four slit apertures 141, 142, 143, 144 illustratively shown in FIG. 7.

The value of α can be plotted from Equation 1 as a function of the x coordinate of the voxel position for each slit aperture 141, 142, 143, 144 in the secondary collimator. The graph 800 plots the curves 803, 804, 805, and 806 of θ for the secondary collimator 100 comprising 4 slits, $1 \leq i \leq 4$, in FIG. 7.

The lowest curve 803 is related to the first slit aperture 141 that is nearest to the x axis. Similarly the next lowest curve 804 is related to the second slit aperture 142. The next lowest curve 805 is related to the third slit aperture 143. The highest curve 806 is related to the fourth slit aperture 144.

The shaded region 807 in the graph 800 represents the range of angles (vertical scale) and the range of positions along the primary beam (horizontal scale) for which measurements are required. For each position along the primary beam 95 (FIG. 7) there are two curves that provide measurements near to the smallest and largest angles required. For example, in this non-limiting example, the curves 803 and 804 cover the x region from the end 808 of the object 12, at 4000 mm from the second radiation source 80 to the vertical line 809 at 3300 mm. The other end 810 of the object 12 is located about 1200 mm from the second radiation source 80. Another vertical line 811 is positioned at about 2000 mm. In like manner, curves 804 and 805 span the region between the two vertical lines 809 and 811. Additionally, curves 805 and 806 span the region from the second vertical line 811 to the end 810 of the object 12.

There is a further relationship between the photon energy, E, the angle of scatter, α, and the momentum transfer, x, as predetermined in the following equation:

Equation 2

$$x_i = \frac{E \cdot \sin\left(\frac{\theta_i}{2}\right)}{1.24} \quad (2)$$

where X is in inverse nanometers when E is expressed in keV.

Referring back to FIGS. 6 and 7, considering any predetermined voxel irradiated by the primary X-ray beam 95, it can scatter into the four secondary collimator slits apertures 141, 142, 143, 144 at four distinct angles of scatter, $\theta_1, \theta_2, \theta_3, \theta_4$. Hence, from Equation 2, it provides simultaneously the XRD intensity at four values of momentum, x. This feature can be used either to increase the signal-to-noise ratio in the measurement, or it can be used to extend the range of momenta values corresponding to a certain photon energy, E. Owing to attenuation effects, only the high energy photons will have appreciable transmission through the container. The multi-angle capability extends the range of momenta for which XRD intensities are measured from a certain range of photon energies. The four narrow bands of XRD intensities over the four different momenta ranges can be synthesized to give a single, broadband.

These principles can be illustrated in the following exemplary and non-limiting way. Assume that an x-ray source having a tip energy of 800 keV is available. Assume further that only the top 250 keV energy band gives useful XRD signal, as the lower energy photons are too strongly absorbed in the container. Finally assume that the highest momentum for which measurements are to be made is 2 $nm^{-1}$. If measurements were made at only a single angle, only the momenta range from 2 $nm^{-1}$ to 1.375 $nm^{-1}$ could be covered. When four angles are available in the ratios 1, (1.375/2), $(1.375/2)^2$ and $(1.375/2)^3$, these ranges increase to: 2 $nm^{-1}$ to 1.375 $nm^{-1}$; 1.375 $nm^{-1}$ to 0.95 $nm^{-1}$; 0.95 $nm^{-1}$ to 0.65 $nm^{-1}$; and 0.65 $nm^{-1}$ to 0.45 $nm^{-1}$. Hence, in this particular non-limiting example, a total range from 2 $nm^{-1}$ down to 0.45 $nm^{-1}$ can be covered. Naturally, this example is provided merely for enablement purposes and to illustrate the scientific and mathematical principles that support embodiments of the invention; accordingly, this example and the numerical values used should not be construed to limit the scope of the appended claims unnecessarily. Instead, it is contemplated that the scope of the appended claims cover any and all applicable numerical values and/or ranges of values that may be associated with embodiments of the invention, or equivalents thereof.

Figure 9:
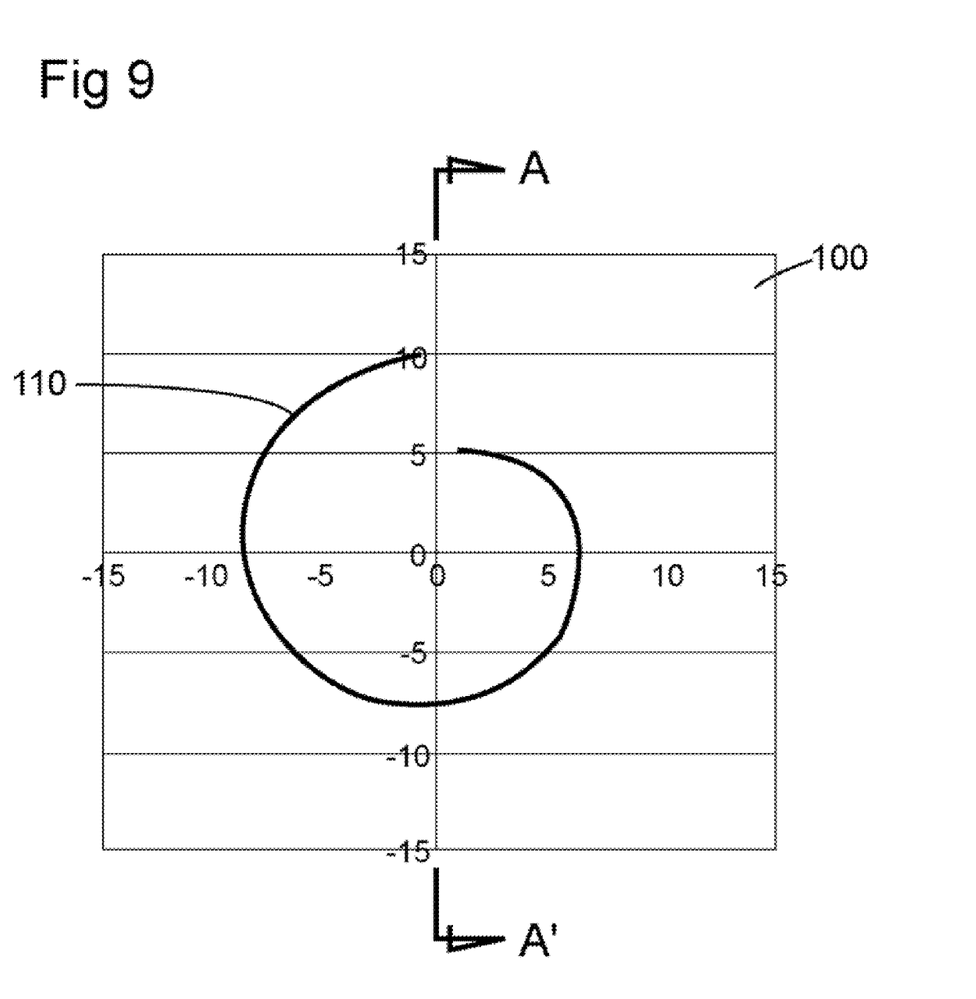
FIG. 9 is a top view of another embodiment of the secondary collimator of FIG. 6, which includes a continuous spiral aperture.

FIG. 9 is a top view of another embodiment of the secondary collimator of FIG. 6, which includes a continuous spiral aperture 110. The above principles are extended to create what is believed to be a novel and inventive secondary multipoint, multiangular collimator of continuous form as shown in FIG. 9. Consider scatter from a certain voxel as it scatters into the spirally-increasing azimuthal angle (clockwise round the spiral). Many more values of scatter angle α than the four described above with respect to FIG. 7 now become available. XRD profiles over a limited energy range can be superimposed on one another to derive a XRD profile over an extended momentum range.

In FIG. 9, the horizontal and vertical scales of the secondary collimator 100 shown are in mm and correspond to the case of a radiation source—collimator distance of about 5 m combined with a photon energy of about 500 keV.

As may be inferred from the above description, the multi-angle capability of the secondary collimator 100 comes from the fact that each ray scattered from a certain voxel varies in scatter angle around the continuous spiral slit aperture 110.

The multipoint capability of the secondary collimator 100 comes from the fact that a 2-D pixellated detector is located behind the collimator, as shown in FIG. 6, and rays from different voxels along the primary beam 95 at one value of azimuthal angle are incident on the detector at different values of its radial coordinate (referred to the primary beam axis).

Figure 10:
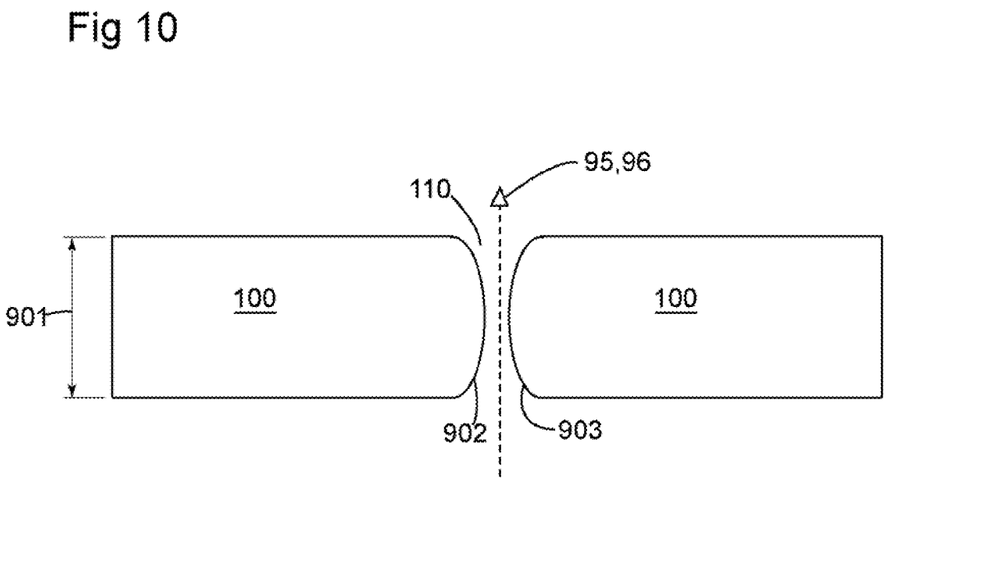
FIG. 10 is a side view, taken along the line A-A' in FIG. 9, of a portion of the continuous spiral aperture.

FIG. 10 is a side view, taken along the line A-A' in FIG. 9, of a portion of the continuous spiral aperture 110. At the very high photon energies that are envisaged for XRD of objects 12

(FIG. 6), the diffraction patterns can only be measured at very small angles of scatter, such as 7×10$^{-3}$ radians. This means that all collimating elements have apertures 110 of sub mm dimensions. At the same time, the collimating elements 110 have to have thicknesses corresponding to tens of mm of a high Z material to give useful absorption of unwanted radiation. A depth profile of a secondary collimator 100 envisaged for this invention is shown in FIG. 10. The body of the secondary collimator 100 may be manufactured by casting a material of high atomic number ("Z"). A non-limiting example of such a material is lead.

In one embodiment, a thickness 901 of the secondary collimator 100 is approximately 20 mm. The opposite faces 902, 903 of the secondary collimator slit aperture(s) 110 are rounded. This rounded form reduces X-ray scattering from the faces of the slit aperture(s) 110 that are irradiated by a primary beam of radiation.

The collimation schemes described herein have good attenuation at the high photon energies required for screening of objects, such as but not limited to, shipping containers, while demonstrating high angular resolution.

Embodiments of the secondary collimator 100 described above, with respect to FIGS. 6, 7, 8, 9, and 10 are mechanically easy to manufacture while having the very high angular resolution needed to measure X-ray diffraction profiles using photons of very high energy (sub MeV). Moreover, embodiments of the secondary collimator 100 enable a plurality of voxels (multipoint) along the primary beam 95 to be investigated simultaneously, whereas a single-point XRD-based threat detection system can analyze only one voxel. Additionally, the multiangle capability of embodiments of the second detection system 11 allows XRD profiles to be measured from a predetermined energy band of photons over a wider range of momenta than is possible with just a single angle. This increases the scatter photon flux.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

As used herein, an element or function recited in the singular and proceeded with the word "a" or "an" should be understood as not excluding plural said elements or functions, unless such exclusion is explicitly recited. Furthermore, references to "one embodiment" of the claimed invention should not be interpreted as excluding the existence of additional embodiments that also incorporate the recited features.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. For example, although embodiments of the invention have been described with reference to X-ray sources and X-ray detectors, other types of radiation may be used. Other embodiments will occur to those skilled in the art and are within the scope of the following claims.

What is claimed is:

1. A secondary collimator, comprising:
a body formed of a high density material; and
a continuous spiral slit aperture formed in the body, wherein the continuous spiral slit aperture is oriented with a spirally increasing azimuth angle to enable multiple scatter beams to simultaneously pass through the continuous spiral slit aperture at different scatter angles for extending a range of momenta for which x-ray diffraction (XRD) intensities are measured for a predetermined range of photon intensities.

2. The secondary collimator of claim 1, wherein a first predetermined scatter angle with respect to an axis of the secondary collimator and a second predetermined scatter angle with respect to the axis enables a first scatter detector and a second scatter detector to respectively capture photons scattered from a scan area of an object along predetermined ray paths that pass through the continuous spiral slit aperture.

3. The secondary collimator of claim 1, wherein at least one predetermined scatter angle satisfies:

$$\theta_i = \tan^{-1}\left(\frac{a_i}{S - x_v}\right)$$

wherein, $a_i$ is a distance of an ith portion of the continuous spiral slit aperture from an axis of the secondary collimator; S is a position (x coordinate) of the secondary collimator to an x-ray source; and $x_v$ is an x coordinate of a voxel in which scattering originates.

4. A threat detection system comprising:
an x-ray source configured to irradiate an object; and
a secondary collimator positioned apart from the x-ray source, the secondary collimator comprising:
a body formed of a high density material; and
a continuous spiral slit aperture formed in the body, wherein the continuous spiral slit aperture is oriented with a spirally increasing azimuth angle to enable multiple scatter beams to simultaneously pass through the continuous spiral slit aperture at different scatter angles for extending a range of momenta for which x-ray diffraction (XRD) intensities are measured for a predetermined range of photon intensities.

5. The threat detection system of claim 4, wherein a first predetermined scatter angle with respect to an axis of the secondary collimator and a second predetermined scatter angle with respect to the axis enables a first scatter detector and a second scatter detector to respectively capture photons scattered from a scan area of an object along predetermined ray paths that pass through the continuous spiral slit aperture.

6. The threat detection system of claim 4, wherein at least one predetermined scatter angle satisfies:

$$\theta_i = \tan^{-1}\left(\frac{a_i}{S - x_v}\right)$$

wherein, $a_i$ is a distance of an ith portion of the continuous spiral slit aperture from an axis of the secondary collimator; S is a position (x coordinate) of the secondary collimator to an x-ray source; and $x_v$ is an x coordinate of a voxel in which scattering originates.

7. The threat detection system of claim 4, further comprising a plurality of x-ray detectors positioned apart from the x-ray source, wherein the plurality of x-ray detectors comprises a first detector positioned along an axis parallel to a primary beam of radiation and a first scatter detector and a second scatter detector positioned between the first detector and the x-ray source.

8. The threat detection system of claim 7, wherein the secondary collimator is positioned between the first scatter detector and the second scatter detector, the first scatter detector is disposed at a first predetermined scatter angle with respect to the axis and the second scatter detector is disposed at a second predetermined scatter angle with respect to the axis to capture photons scattered from a scan area of the object along predetermined ray paths that pass through the continuous spiral slit aperture.

9. A method comprising:
   irradiating an object with an x-ray beam using an x-ray source;
   focusing scatter beams of the x-ray beam using a secondary collimator, wherein the secondary collimator includes a continuous spiral slit aperture that is oriented with a spirally increasing azimuth angle to enable multiple scatter beams to simultaneously pass through the continuous spiral slit aperture at different scatter angles for extending a range of momenta for which x-ray diffraction (XRD) intensities are measured for a predetermined range of photon intensities; and
   detecting photons in the scatter beams using at least one scatter detector.

10. The method of claim 9, wherein the at least one scatter detector includes a first scatter detector and a second scatter detector, said detecting photons comprises:
   detecting at the first scatter detector photons scattered from a scan area of the object along a first path having a first predetermined scatter angle with respect to an axis of the secondary collimator; and
   detecting at the second scatter detector photons scattered from the scan area of the object along a second path having a second predetermined scatter angle with respect to the axis, wherein each of the first path and the second path pass through the continuous spiral slit aperture.

11. The method of claim 9, wherein at least one predetermined scatter angle satisfies:

$$\theta_i = \tan^{-1}\left(\frac{a_i}{S - x_v}\right)$$

wherein, $a_i$ is a distance of an ith portion of the continuous spiral slit aperture from an axis of the secondary collimator; S is a position (x coordinate) of the secondary collimator to the x-ray source; and $x_v$ is an x coordinate of a voxel in which scattering originates.

* * * * *